(12) United States Patent
Nopasri

(10) Patent No.: US 10,039,443 B2
(45) Date of Patent: Aug. 7, 2018

(54) BLADE AID

(71) Applicant: Randolph P Nopasri, La Mesa, CA (US)

(72) Inventor: Randolph P Nopasri, La Mesa, CA (US)

( * ) Notice: Subject to any disclaimer, the term of this patent is extended or adjusted under 35 U.S.C. 154(b) by 461 days.

(21) Appl. No.: 14/734,110

(22) Filed: Jun. 9, 2015

(65) Prior Publication Data

US 2015/0351622 A1    Dec. 10, 2015

Related U.S. Application Data

(60) Provisional application No. 62/009,002, filed on Jun. 6, 2014.

(51) Int. Cl.
*A61B 1/267* (2006.01)
*A61B 13/00* (2006.01)
*A61B 1/00* (2006.01)

(52) U.S. Cl.
CPC .......... *A61B 1/267* (2013.01); *A61B 1/00135* (2013.01); *A61B 13/00* (2013.01)

(58) Field of Classification Search
CPC ..................................................... A61F 13/00
USPC ............................... 602/41–77; 128/893–894
See application file for complete search history.

(56) References Cited

U.S. PATENT DOCUMENTS

| | | | | |
|---|---|---|---|---|
| 876,022 | A * | 1/1908 | Schiffhauer | A61F 13/063 128/894 |
| 1,736,515 | A * | 11/1929 | Anderson | A61F 13/063 128/894 |
| 2,069,034 | A * | 1/1937 | Hicks | A61F 13/063 128/894 |
| 2,539,115 | A * | 1/1951 | Brachman | A61F 13/063 128/894 |
| 2,897,961 | A * | 8/1959 | Bush | A61F 13/0203 206/441 |
| 3,029,813 | A * | 4/1962 | Hanington | A61F 13/063 128/894 |
| 3,342,183 | A * | 9/1967 | Edenbaum | A61L 15/44 424/448 |
| 3,426,749 | A * | 2/1969 | Jephcott | A61B 1/00142 206/363 |
| 4,583,527 | A * | 4/1986 | Musicant | A61B 1/267 600/195 |
| 4,834,077 | A * | 5/1989 | Sun | A61B 1/00142 600/186 |
| 4,878,486 | A * | 11/1989 | Slater | A61B 1/00142 206/438 |
| 5,065,738 | A * | 11/1991 | Van Dam | A61B 1/00142 600/185 |
| 5,438,976 | A * | 8/1995 | Nash | A61B 1/267 600/186 |
| 5,743,849 | A * | 4/1998 | Rice | A61B 1/00142 600/186 |

(Continued)

*Primary Examiner* — Zade Coley

(74) *Attorney, Agent, or Firm* — Michael R Shevlin

(57) ABSTRACT

A tongue control tape for use with a laryngoscope blade having a cotton elastic cloth tape having a length and a width, an adhesive or other bonding means capable of attaching the cotton elastic cloth tape to the laryngoscope blade, and an aperture or window shaped to fit over a portion of the laryngoscope. The tongue control tape provides traction and leverage control over a patients tongue and may be provided in a package or on a roll.

7 Claims, 1 Drawing Sheet

(56) References Cited

U.S. PATENT DOCUMENTS

| | | | | |
|---|---|---|---|---|
| 5,762,623 A * | 6/1998 | Murphy | ............... | A61F 13/023 |
| | | | | 602/75 |
| 5,772,623 A * | 6/1998 | Conte | ............... | A61F 13/0206 |
| | | | | 602/57 |
| 5,861,348 A * | 1/1999 | Kase | ............... | A61F 13/025 |
| | | | | 428/195.1 |
| 6,191,338 B1 * | 2/2001 | Haller | ............... | A61F 13/0206 |
| | | | | 602/43 |
| 6,375,639 B1 * | 4/2002 | Duplessie | ............ | A61M 25/02 |
| | | | | 128/DIG. 26 |
| 7,458,932 B2 * | 12/2008 | Sun | ............... | A61B 1/0008 |
| | | | | 600/185 |
| 7,695,433 B2 * | 4/2010 | Simons | ............... | A61B 1/267 |
| | | | | 600/185 |
| 8,100,857 B2 * | 1/2012 | Kuracina | ............. | A61M 5/158 |
| | | | | 604/110 |
| 2004/0122292 A1 * | 6/2004 | Dey | ............... | A61B 1/0676 |
| | | | | 600/190 |
| 2005/0124859 A1 * | 6/2005 | Sun | ............... | A61B 1/0008 |
| | | | | 600/194 |
| 2007/0027429 A1 * | 2/2007 | Kuracina | ............. | A61M 5/158 |
| | | | | 604/116 |

* cited by examiner

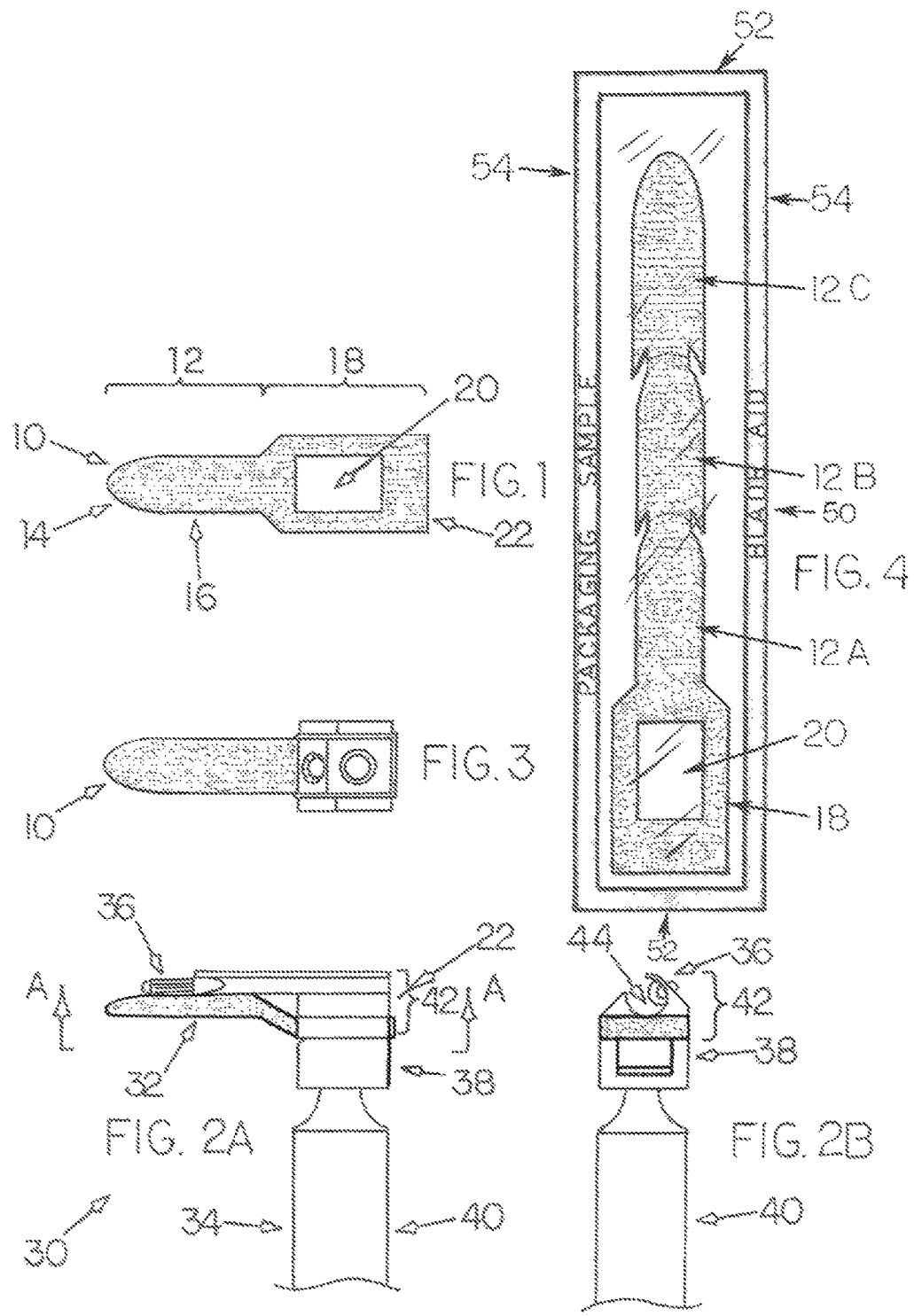

BLADE AID

CROSS-REFERENCE TO RELATED APPLICATIONS

This application claims the benefit of U.S. Provisional Patent Application No. 62/009,002, the entirety of which is incorporated by reference herein.

FIELD

The present invention is generally related to laryngoscopes, and more particularly, to a tongue control tape which is affixed to the underside of a laryngoscopes blade and is used to create traction and controllability over the tongue of a patient during intubation.

BACKGROUND

Tracheal intubation, usually simply referred to as intubation, is the placement of a flexible plastic tube into the trachea (windpipe) to maintain an open airway or to serve as a conduit through which to administer certain drugs. It is frequently performed in critically injured, ill or anesthetized patients to facilitate ventilation of the lungs, including mechanical ventilation, and to prevent the possibility of asphyxiation or airway obstruction. The most widely used route is orotracheal, in which an endotracheal tube is passed through the mouth and vocal cords into the trachea.

Because it is an invasive and extremely uncomfortable medical procedure, intubation is usually performed after administration of general anesthesia and a neuromuscular-blocking drug. It can however be performed in the awake patient with local or topical anesthesia, or in an emergency without any anesthesia at all. Intubation is normally facilitated by using a laryngoscope.

During an emergency procedure, tracheal intubation is often very difficult, leading to repeated laryngoscopic attempts. Repeated conventional tracheal intubation attempts may contribute to patient morbidity. (Mort TC, Emergency tracheal intubation: Complications associated with repeated laryngoscopic attempts. Anesth Analg. 2004; 99:607-13.).

In emergent situations in the Delivery Room and the NICU, there is sometimes trouble intubating babies, a live saving procedure. The oral cavity is often times bloody and/or slick from oral secretions even after sufficient suctioning making it sometimes difficult to gain control over the large muscular tongue. In addition, the use of analgesics or neuromuscular block medications may not be effective or contraindicated in some babies makes it even more difficult.

In view of this, it would be desirable to develop something that can be used with, or affixed to, a laryngoscope blade to gain control over the tongues anatomy during intubation.

SUMMARY

It is an object of the invention to provide an inexpensive implement that helps the health care worker to gain control over a patients tongue during intubation attempts. The tongues physiology, sometimes slippery with blood or secretions, presents a challenge to successful intubation, especially in emergent or conditions when neuromuscular-blocking drugs are contraindicated for use. This tape provides a tactile surface that the tongues papillae readily grip or adhere to, giving the health care worker an aid in controlling the movements of the tongue and helps to reduce lacerations to upper airway tissues.

BRIEF DESCRIPTION OF THE DRAWINGS

FIG. 1 is a top view of a tongue control tape.

FIGS. 2A and 2B are a side view and end views of a laryngoscope scope and blade with the tongue control tape of FIG. 1 mounted on a laryngoscope blade.

FIG. 3 is an underside view of a laryngoscope blade/mast showing the adhesive elastic tape of FIG. 1 mounted on the laryngoscope blade.

FIG. 4 shows one embodiment of packaging for the tongue control tape.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The disclosed invention is an innovative method and mechanism for controlling a tongue during intubation by using a tape applied to a blade of a laryngoscope. One suitable type of tape is a cotton elastic cloth tape with a rubber based adhesive, such as ELASTIKON Elastic Adhesive Tape. The porous construction allows skin to breathe and allows for moisture transmission. The rubber based adhesive provides strong adhesion with minimal residue. The tape is capable of high twist and may conform to many shapes of laryngoscope blades. The tape may have a porous construction that can create traction or friction with the tongue and allow controllability over the tongue by the user when the taped blade is placed against the tongue. The rubber based adhesive provides strong adhesion to the blade with minimal residue and will not come off when wet. The adhesive may be applied to within ⅛" of the tape edge to provide neat and comfortable application without adhesive bleed.

FIG. 1 shows a tongue control tape 10 having a forward or distal portion 12 with the general shape of a laryngoscope blade with rounded forward or distal end 14 and straight sides 16. The tape 10 further includes a proximal portion 18 with an aperture or window 20 shaped to fit over a portion of the laryngoscope (discussed below). The tape 10 may be made of a cotton elastic cloth tape with an adhesive or other bonding means to attach it to the laryngoscope blade. In some embodiments, the tape section that is applied to the blade of the laryngoscope is available in perforated pre-cut lengths 12a, 12b, 12c that the user can simply remove for the desired length 12 appropriate to the dimension of blade laryngoscope they are using (see FIG. 4). The cotton elastic cloth tape may be a porous or open pore material that can create traction or friction along with "Moisture Transmission" properties that work with tongue anatomy and physiology; also preventing the laryngoscope blade from sliding, even when wet. The adhesive may be any pressure-sensitive adhesive providing holding power along the entire length of the distal portion 12 so that a firm bond is established with the laryngoscope blade to prevent accidental separation of the tape 10 and the laryngoscope blade. The adhesive should have sufficient holding power to secure the tape 10 to the laryngoscope blade under the forces encountered during the intubation process. The adhesive may be a rubber based adhesive. A suitable tape is the ELASTIKON Elastic Adhesive Tape from Johnson & Johnson.

As a safety feature, the proximal portion 18 of the tape 10 includes tape portion 22 with the aperture or window 20 shaped to fit over a portion of the laryngoscope. In case the adhesive should fail, the tape portion 22 around the laryngoscope would prevent the tape from aspirating or ingestion during the intubation process.

The tongue control tape 10 is generally a flat, pliable sheet of material with an adhesive side. The adhesive may be covered with a removable material, similar to a band aid. In some embodiments, the tongue control tape 10 may be packaged in similar to a band aid (see FIG. 4). In some embodiments, the tongue control tape 10 may be packaged in sterile packaging or surgically clean packaging. In other embodiments, the tongue control tape 10 may be a continuous roll of tape in which an individual tongue control tape 10 may be removed from the roll, for example by tearing or cutting.

FIGS. 2A and 2B show a partial side view and end view of a laryngoscope 30 having a blade 32, a handle 34 and a light 36. The handle 34 includes a top support 38 that couples with the housing 40 and blade mast 42. The housing 40 may hold one or more batteries to power the light 36. The light 36 extends along the blade 32 and is electrically connected to the handle and the one or more batteries. The blade 32 may be different shapes and sizes suitable for the procedure, including sizes for infants and children. It is desirable that the blade 32 is be made of a material that is durable and easy to clean, such as stainless steel.

Generally, the blade 32 is curved transversely from the edge of the blade 32. The forward or distal portion 12 of the tape 10 is affixed to the underside of the blade 32, as shown in FIG. 3. The blade 32 is used to roll the tongue of a patient out of the way and allow the laryngoscopist to sight under the arc of the blade 32. In some embodiments, the blade 32 may be straight (shown in FIG. 2A), may be curved longitudinally, or may be a combination of curvature and straight configuration, known to those of ordinary skill in the art.

When intubation is to be performed, the user determines the size blade to perform the procedure, selects the appropriate tongue control tape 10 length, removes the protective cover from the adhesive, secures the tongue control tape 10 to the blade and loops the tape portion 22 around the laryngoscope. The user then proceeds with the procedure using the tongue control tape 10 to control the tongue while intubating.

FIG. 4 shows one embodiment of a package 50 suitable for storing and dispensing adhesive strips or bandages. The tongue control tape 10 is contained within an envelope formed by opposed upper and lower sheets. The upper sheet superposes (or substantially superposes) the lower sheet and is releasably attached thereto along the outer perimeter of the package. The lower sheet may have a release liner secured thereto to protect the adhesive side of the tongue control tape 10 while it is within the package. The upper sheet may be made of a clear material for viewing the tongue control tape 10 within the package.

The upper and lower sheets have end regions 52 and edge regions 54. Both the upper sheet and the lower sheet may be joined along the end regions and edge regions with an adhesive or other suitable means is used to bond the upper sheet to the lower sheet. This may also provide a sterile seal if desired. The upper and lower sheets may also have an area without adhesive defining a pull cover. In this embodiment, the upper sheet superposes the lower sheet and except for a portion which forms a first tab and a second tab, is releasably attached thereto along the outer perimeter of the package. To open, the user grasps the first and second tabs and pulls the upper and lower sheets, exposing the tongue control tape 10. This is similar to a band aid package.

In other embodiments, the tongue control tape 10 may be in a roll, similar to the ELASTIKON Elastic Adhesive Tape roll. In this embodiment, each tongue control tape 10 may be attached to each other at their ends and separated as needed.

While the above embodiments describe the tongue control tape 10 for use in humans, it is also envisioned that the tongue control tape 10 may also compatible with veterinary use.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth hereinbelow not be construed as being order-specific unless such order specificity is expressly stated in the claim.

The invention claimed is:

1. An apparatus for use during intubation to help control the tongue comprising:
    a laryngoscope having a blade and a handle, the blade having a distal free end and a proximal end;
    a cotton elastic cloth tape having;
        a distal portion with a distal end in the general shape of the laryngoscope blade;
        a proximal portion having an aperture or window shaped to fit around a portion of the laryngoscope to prevent the tape from aspirating or ingestion during the intubation process; and
        an adhesive side and a tongue control side;
    wherein, in an assembled configuration a blade mast extends through aperture or window and the adhesive side of the tape engages the laryngoscope blade and the tongue control side is configured to frictionally engage the tongue to prevent the laryngoscope blade from sliding.

2. The apparatus of claim 1, wherein the length is adjustable to fit different length laryngoscope blades.

3. The apparatus of claim 1, further comprising a package suitable for storing the apparatus, the package comprising an envelope formed by opposed upper and lower sheets releasably attached thereto along an outer perimeter of the package.

4. The apparatus of claim 1, wherein the tape is
    a precut length of elastic tape including the adhesive side and non adhesive side, and
    removable tabs positioned onto the adhesive side.

5. The apparatus of claim 4, wherein the precut adhesive tapes will be provided in surgically clean packaging which is ready for mounting onto a laryngoscope blade and it's mounting area.

6. The apparatus of claim 4, wherein the aperture of the precut tape is used for locating and positioning the apparatus over the mast.

7. The apparatus of claim 1, wherein the elastic tape is made of a material configured to create traction or friction with the tongue.

\* \* \* \* \*